United States Patent
Hamel-Bissell et al.

(10) Patent No.: US 11,763,490 B2
(45) Date of Patent: Sep. 19, 2023

(54) CAROUSEL GUIDANCE FOR OPTICAL IMAGING DEVICES

(71) Applicant: Optos plc, Dunfermline (GB)

(72) Inventors: Brendan Hamel-Bissell, San Francisco, CA (US); Benjamin Adam Jacobson, Santa Barbara, CA (US); Clint Suson, San Francisco, CA (US); Clark Pentico, Simi Valley, CA (US); Andre E. Adams, Tiburon, CA (US); Tushar M. Ranchod, Berkeley, CA (US)

(73) Assignee: Optos plc, Dunfermline (GB)

( * ) Notice: Subject to any disclaimer, the term of this patent is extended or adjusted under 35 U.S.C. 154(b) by 0 days.

(21) Appl. No.: 16/936,891

(22) Filed: Jul. 23, 2020

(65) Prior Publication Data

US 2021/0027494 A1    Jan. 28, 2021

Related U.S. Application Data

(60) Provisional application No. 62/877,766, filed on Jul. 23, 2019.

(51) Int. Cl.
*G06T 7/80* (2017.01)
*H04N 17/00* (2006.01)
(Continued)

(52) U.S. Cl.
CPC ............... *G06T 7/80* (2017.01); *G06T 5/50* (2013.01); *H04N 17/002* (2013.01);
(Continued)

(58) Field of Classification Search
CPC . G06T 2207/20221; G06T 2207/30201; G06T 3/4038; G06T 5/50; G06T 7/80;
(Continued)

(56) References Cited

U.S. PATENT DOCUMENTS 9,762,651 B1    9/2017  Sharifi
9,898,082 B1*   2/2018  Greenwald ............. G06F 3/013
(Continued)

FOREIGN PATENT DOCUMENTS

JP    6209448 B2    9/2017
JP    6209448 B2    10/2017
(Continued)

OTHER PUBLICATIONS

International Search Report and Written Opinion issued in corresponding application No. PCT/US2020/043339, dated Oct. 20, 2020.

(Continued)

*Primary Examiner* — James T Boylan
(74) *Attorney, Agent, or Firm* — Faegre Drinker Biddle & Reath

(57) ABSTRACT

Method of aligning an imaging device with respect to an object, the imaging device comprising two or more optical channels, is disclosed. The method may include aiming the two or more optical channels at corresponding overlapping zones of the object such that the two or more optical channels are oriented at different angles relative to each other and off-axis relative to a central axis of the imaging device. The method may additionally include guiding or focusing the imaging device relative to the object using composite images created by combining separate images from the two or more optical channels.

20 Claims, 10 Drawing Sheets

(51) Int. Cl.
  *G06T 5/50* (2006.01)
  *H04N 23/56* (2023.01)
  *H04N 23/67* (2023.01)

(52) U.S. Cl.
  CPC ............ *H04N 23/56* (2023.01); *H04N 23/67* (2023.01); *G06T 2207/20221* (2013.01); *G06T 2207/30201* (2013.01)

(58) Field of Classification Search
  CPC ............ H04N 17/002; H04N 5/2256; H04N 5/23212; H04N 5/23229; H04N 5/23293; H04N 5/247
  See application file for complete search history.

(56) References Cited

U.S. PATENT DOCUMENTS

| | | | |
|---|---|---|---|
| 2013/0271728 A1* | 10/2013 | Ranchod | A61B 3/12 351/206 |
| 2014/0049749 A1 | 2/2014 | Levecq | |
| 2015/0004558 A1* | 1/2015 | Inglese | A61B 6/5235 433/29 |
| 2016/0235292 A1* | 8/2016 | Gramatikov | A61B 3/1225 |
| 2016/0262613 A1* | 9/2016 | Klin | A61B 5/163 |
| 2018/0012336 A1* | 1/2018 | Cao | G06T 3/4038 |
| 2019/0059715 A1* | 2/2019 | Lamba | G06T 5/50 |
| 2019/0113423 A1 | 4/2019 | Goodman | |
| 2019/0200856 A1 | 4/2019 | Ranchod | |
| 2019/0231459 A1* | 8/2019 | Mustufa | A61B 34/25 |
| 2021/0385431 A1 | 12/2021 | Ohyama | |
| 2022/0019091 A1* | 1/2022 | Nobis | G02C 11/04 |

FOREIGN PATENT DOCUMENTS

| | | |
|---|---|---|
| WO | 2018/051743 A1 | 3/2018 |
| WO | 2018051743 A1 | 3/2018 |

OTHER PUBLICATIONS

International Preliminary Report on Patentability dated Oct. 20, 2020 in International App. No. PCT/US2020/043339 (9 sheets).

* cited by examiner

CAROUSEL GUIDANCE FOR OPTICAL IMAGING DEVICES

CROSS-REFERENCE TO RELATED APPLICATION

This patent application claims the benefit of and priority to U.S. Provisional App. No. 62/877,766 filed Jul. 23, 2019, which is incorporated by reference in the present disclosure in its entirety for all that it discloses.

FIELD

The application relates generally to methods for guiding and aligning optical imaging systems.

BACKGROUND

Traditional fundus cameras have a single imaging pathway and provide live video from a single sensor which is also used for still image capture. This imaging pathway is used to provide live video during the guidance or alignment phase that precedes image acquisition. For video guidance to be useful, the guidance video should provide feedback for the operator regarding centration and alignment as well as image focus and quality.

The subject matter claimed herein is not limited to embodiments that solve any disadvantages or that operate only in environments such as those described above. Rather, this background is only provided to illustrate one example technology area where some embodiments described herein may be practiced.

SUMMARY

Example 1—One or more embodiments of the present disclosure may include a method of aligning an imaging device with respect to an object, the imaging device comprising two or more optical channels. The method may include aiming the two or more optical channels at corresponding overlapping zones of the object such that the two or more optical channels are oriented at different angles relative to each other and off-axis relative to a central axis of the imaging device. The method may additionally include guiding or focusing the imaging device relative to the object using composite images created by combining separate images from the two or more optical channels.

Example 2—In accordance with one or more embodiments of the present disclosure, any of the methods disclosed herein, such as that in Example 1, may further include centering the imaging device using images from outer and inner peripheries of fields of view of the optical channels.

Example 3—In accordance with one or more embodiments of the present disclosure, for any of the methods disclosed herein, such as that in Example 2, the images from the outer and inner peripheries may be used to generate the composite images.

Example 4—In accordance with one or more embodiments of the present disclosure, for any of the methods disclosed herein, such as that in Examples 1-3, the object to be imaged is an eye and the imaging device is aligned using corneal reflections of illumination from the two or more optical channels.

Example 5—In accordance with one or more embodiments of the present disclosure, for any of the methods disclosed herein, such as that in Example 4, a fixation target is located between the optical channels, the fixation target including a target for the eye to focus upon while the eye is imaged.

Example 6—In accordance with one or more embodiments of the present disclosure, for any of the methods disclosed herein, such as that in any of Examples 1-5, the two or more optical channels include a first and a second optical channel, and guiding or focusing the imaging device further includes illuminating a cross-channel region of the first optical channel via the second optical channel, and capturing one of the separate images as a cross-channel image of the cross-channel region of the first optical channel via the first optical channel while the second optical channel is illuminating the cross-channel region, where the cross-channel image is used to generate the composite images Example 7—In accordance with one or more embodiments of the present disclosure, any of the methods disclosed herein, such as that in Example 6, may further include illuminating at least one of an outer and an inner periphery of a field of view of the first optical channel while the second optical channel illuminates the cross-channel region.

Example 8—In accordance with one or more embodiments of the present disclosure, any of the methods disclosed herein, such as that in Example 6 or 7, may further include, after capturing the cross-channel image, illuminating a second cross-channel region of the second optical channel via the first optical channel. Such a method may also include capturing a second cross-channel image of the second cross-channel region of the second optical channel via the second optical channel while the first optical channel is illuminating the second cross-channel region, and generating a second composite image using the second cross-channel image.

Example 9—In accordance with one or more embodiments of the present disclosure, any of the methods disclosed herein, such as that in Example 8, may further include updating a display previously presenting one or more of the composite images to the second composite image to create a video on the display.

Example 10—In accordance with one or more embodiments of the present disclosure, any of the methods disclosed herein, such as that in Example 9, may further include repeatedly generating additional composite images and updating the display with the additional composite images, where the updating of the display creates a carousel effect as different regions of the video are updated based on which of the two or more optical channels captures sub-images contributing to the additional composite images.

Example 11—In accordance with one or more embodiments of the present disclosure, any of the methods disclosed herein, such as that in Example 1-10, guiding or focusing the imaging device may further include performing initial guidance based on a first set of the composite images representing at least an inner periphery region of an eye as the imaging device is a first distance away from the eye; performing secondary guidance based on a second set of the composite images representing at least an outer periphery region of the eye as the imaging device transitions from the first distance to a second distance away from the eye closer than the first distance; and performing final guidance or focusing based on a third set of the composite images representing at least a cross channel region of the eye as the imaging device is at the second distance away from the eye.

Example 12—In accordance with one or more embodiments of the present disclosure, any of the methods disclosed herein, such as that in Example 1-11, guiding or focusing the imaging device may further include performing initial guidance based on corneal reflections of illumination from the two or more optical channels off of a cornea of an eye as the imaging device is a first distance away from the eye; performing secondary guidance based on a first set of the composite images representing at least inner and outer periphery regions of the eye as the imaging device transitions from the first distance away from the eye to a second distance away from the eye closer than the first distance; and performing final guidance or focusing based on a second set of the composite images representing both a cross channel region and the inner periphery region of the eye as the imaging device is at the second distance away from the eye.

Example 13—In accordance with one or more embodiments of the present disclosure, any of the methods disclosed herein, such as that in Example 1-12, guiding or focusing the imaging device may further include performing initial guidance based on a first set of the composite images representing at least cross channel regions of an eye as the imaging device is a first distance away from the eye; and performing final guidance or focusing based on a second set of the composite images representing at least an outer periphery region of the eye as the imaging device is at a second distance away from the eye closer than the first distance.

Example 14—In accordance with one or more embodiments of the present disclosure, any of the methods disclosed herein, such as that in Example 1-13, guiding or focusing the imaging device may further include concurrently displaying both a first subset of the composite images representing cross channel regions of an eye and a second subset of the composite images representing an outer periphery region of the eye.

Example 15—In accordance with one or more embodiments of the present disclosure, any of the methods disclosed herein, such as that in Example 1-14, guiding or focusing the imaging device may further include concurrently displaying both a first subset of the composite images representing cross channel regions of an eye and an indirect graphic based on an outer periphery region of the eye.

Example 16—In accordance with one or more embodiments of the present disclosure, for any of the methods disclosed herein, such as that in Example 15, the indirect graphic includes at least one of status bars and a dot within a circle Example 17—One or more additional embodiments of the present disclosure may include an imaging device. The imaging device may include a first optical channel including a first illumination source and a first image capturing device, where the first optical channel is set at a first off-axis position relative to a central axis of the imaging device. The imaging device may also include a second optical channel including a second illumination source and a second image capturing device, where the second optical channel is set at a second off-axis position relative to the central axis, and where the second off-axis position is positioned such that the first optical channel and the second optical channel are directed towards corresponding overlapping zones in line with the central axis. The imaging device may further include a display, one or more processors, and one or more non-transitory computer-readable media containing instructions which, when executed, are configured to cause the imaging device to perform operations. The operations may include capturing one or more images via the first image capturing device and the second image capturing device, generating composite images using the captured images, and displaying the composite images while guiding or focusing the imaging device relative to an object to be imaged.

Example 18—In accordance with one or more embodiments of the present disclosure, any of the imaging devices disclosed herein, such as that in Example 17, may further include a fixation target located between the first and the second optical channels, the fixation target including a target for an eye to focus upon while the eye is imaged when the eye is the object to be imaged.

Example 19—In accordance with one or more embodiments of the present disclosure, any of the imaging devices disclosed herein, such as that in Examples 17-18, may further include a third optical channel aligned with the central axis.

Example 20—In accordance with one or more embodiments of the present disclosure, for any of the imaging devices disclosed herein, such as that in Examples 17-19, the guiding or focusing may be performed manually be a user of the imaging device.

BRIEF DESCRIPTION OF FIGURES

Example embodiments will be described and explained with additional specificity and detail through the use of the accompanying drawings in which.

DESCRIPTION OF EMBODIMENTS

Figure 1:
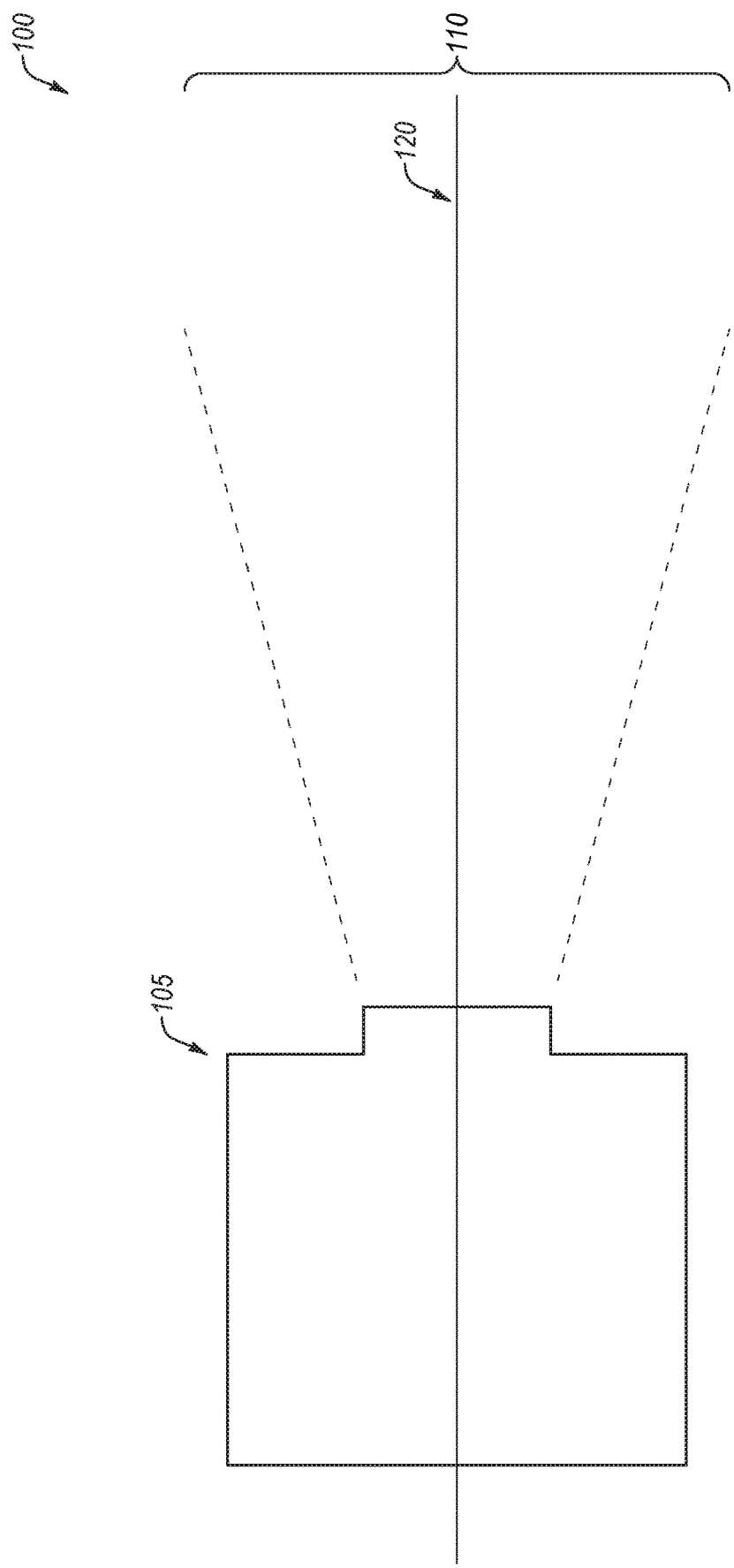
FIG. 1 illustrates an example implementation of an optical device.

The present disclosure relates to, inter alia, the use of images from multiple disparate optical imaging channels to align an optical imaging device. Cross channel optical imaging devices eliminate imaging artifacts by using multiple optical channels, but with multiple optical channels viewing the same object from different angles, no single optical channel can provide video that is sufficient for aligning the optical imaging device. Unlike single-channel optical imaging devices, rotationally symmetric or non-coaxial multi-channel optical imaging devices may not have a single imaging channel that is aligned along the central axis of the imaging device. Therefore, no single channel is able to provide a live video or single frame view that is rotationally symmetric and coaxial with the central axis of the device. The present disclosure provides a method to align the optical imaging device with the images to be captured in the context of a multi-channel imaging device. For example, composite images may be created from cross channel regions of optical channels where illumination is provided by a first optical channel and imaging is performed by a second optical channel, and whereby imaging by the first and second optical channels simultaneously is not desirable, or may not be possible, due to in-channel illumination artifacts. The sequential capture of images that include but are not centered on the central axis of the device may then be used to create a composite image that is centered about the central axis of the device. These composite images may be used to guide and focus the optical imaging device. Peripheral images from the outer and inner periphery of the imaging zones of the optical channels may additionally or alternatively be used to provide information for centering the optical imaging device on the object to be imaged. Additionally or alternatively, light from the optical imaging channels reflected off of the object to be imaged may be used to guide the optical imaging device. Aligning multi-channel optical imaging devices is not as simple as aligning a single optical channel, but by using composite images of the center of the field of view of the optical imaging device, peripheral images from each optical channel, and/or reflections off the object to be imaged from the optical channels, cross channel optical imaging devices may be guided, aligned, and centered to capture high-quality images.

By way of explanation of one example, when imaging a retina, an optical imaging device comprising multiple optical channels may be placed in front of a patient's eye. Reflections from the optical channels off the patient's cornea may provide guidance for positioning and/or aligning the optical imaging device. Outer peripheral images may provide information about when the optical pathways of the optical imaging device clear the patient's pupil. Then composite images composed of images from the cross channel regions of all optical channels of the optical imaging device may be used to guide the device to the fovea, or center of the macula, by providing images and or video of macular details. At the same time, inner and/or outer peripheral images may be used to center the optical imaging device. When the device is centered on the retina, the optical channels of the optical imaging device may capture images of the retina using cross channel illumination. In some cases, a fixation target may be located in between the multiple imaging channels to provide the eye a single point on which to focus. Additionally or alternatively, illumination from the optical channels may serve as a fixation target for the patient to look at to hold the patient's eye steady.

FIG. 1 illustrates an example optical device 100 with a single optical imaging channel 105. The optical imaging channel 105 has an optical channel field of view 110 which is rotationally symmetric around the optical channel central axis 120. Such an optical imaging device 100 provides illumination and captures images through the single optical channel 105. The optical device 100 contains a sensor (not illustrated) which provides video for aligning the optical device 100 with the object to be imaged. The optical device 100 is aligned with the object to be imaged along the optical channel central axis 120.

The optical device 100 may be limited in the image capturing capabilities because it is aligned along the optical channel central axis 120. Such an alignment may provide for easier focusing and alignment of the optical device 100 at the expense of illumination interfering with the imaging capabilities of the optical device 100 when capturing meaningful images of the eye, particularly with a greater optical channel field of view 110.

Figure 2:
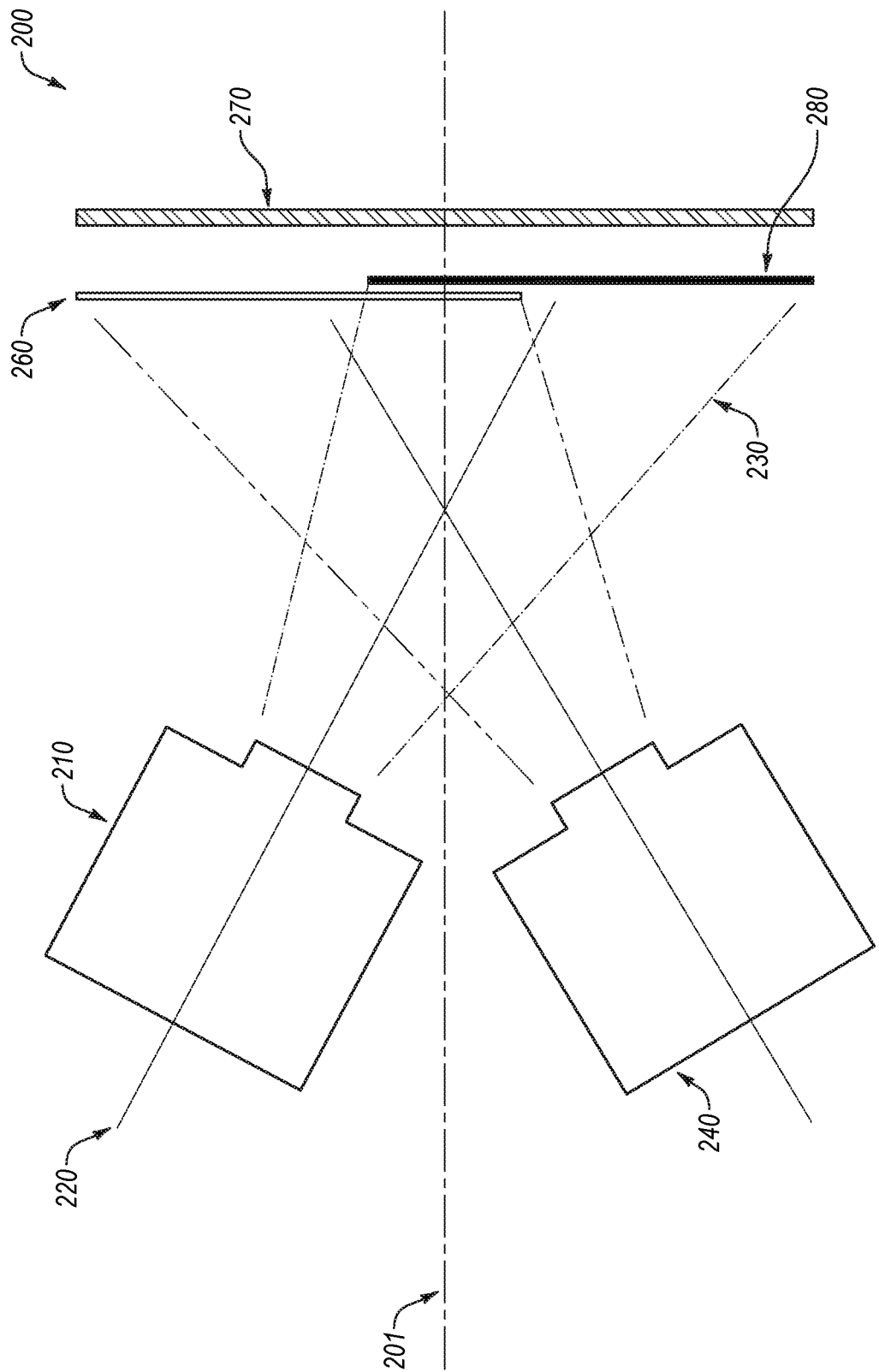
FIG. 2 illustrates an example implementation of a multi-channel imaging device.

FIG. 2 illustrates an example multi-channel optical device 200 in accordance with one or more embodiments of the present disclosure. Optical channel A 210 and optical channel B 240 may be positioned at an angle relative to each other and may image and/or illuminate different zones of an object or scene 270. With reference to the alignment of optical channel A 210 and optical channel B 240, neither optical channel A 210 nor optical channel B 240 is coaxial with the central axis 201 of the device. As such, neither optical channel A 210 nor optical channel B 240 alone is able to provide a rotationally symmetric, approximately centered guidance image to aid users in the positioning and alignment of device 200. For example, the optical channel A 210 may image and/or illuminate a zone Y 280 and the optical channel B 240 may image and/or illuminate a zone X 260. The operation of the optical channels 210 and 240 may be described with reference to the optical channel A 210 as an example, but the description is equally applicable to the optical channel B 240 as well as any other additional optical channels (for example, the multi-channel optical device 200 may include three or more optical channels). As illustrated in FIG. 2, the optical channel A 210 may be oriented and aligned along a central axis 220 which may be directed towards the object or scene 270. Rather than being aligned with a central axis 201 of the optical imaging device 200 such as illustrated in FIG. 1, the central axis 220 may be offset and/or at an angle relative to the central axis 201 of the optical imaging device 200. Additionally or alternatively, because of the offset nature of the optical channel A 210, the zone Y 280 may not cover the entire object or scene 270 to be imaged. Thus, images and video from the optical channel A 210 alone may not adequately provide guidance when aligning the optical imaging device 200.

Modifications, additions, or omissions may be made to the optical imaging device 200 without departing from the scope of the present disclosure. For example, the optical imaging device 200 may include more or fewer elements than those illustrated in FIG. 2. For example, the optical imaging device 200 may include any number of optical channels. As another example, the optical imaging device 200 may include additional channels that are co-axial with the device central axis. As an additional example, the optical imaging device 200 may include channels that are not co-axial with the device central axis 201 but which are not rotationally symmetric with regard to the device central axis 201.

Figure 3A:
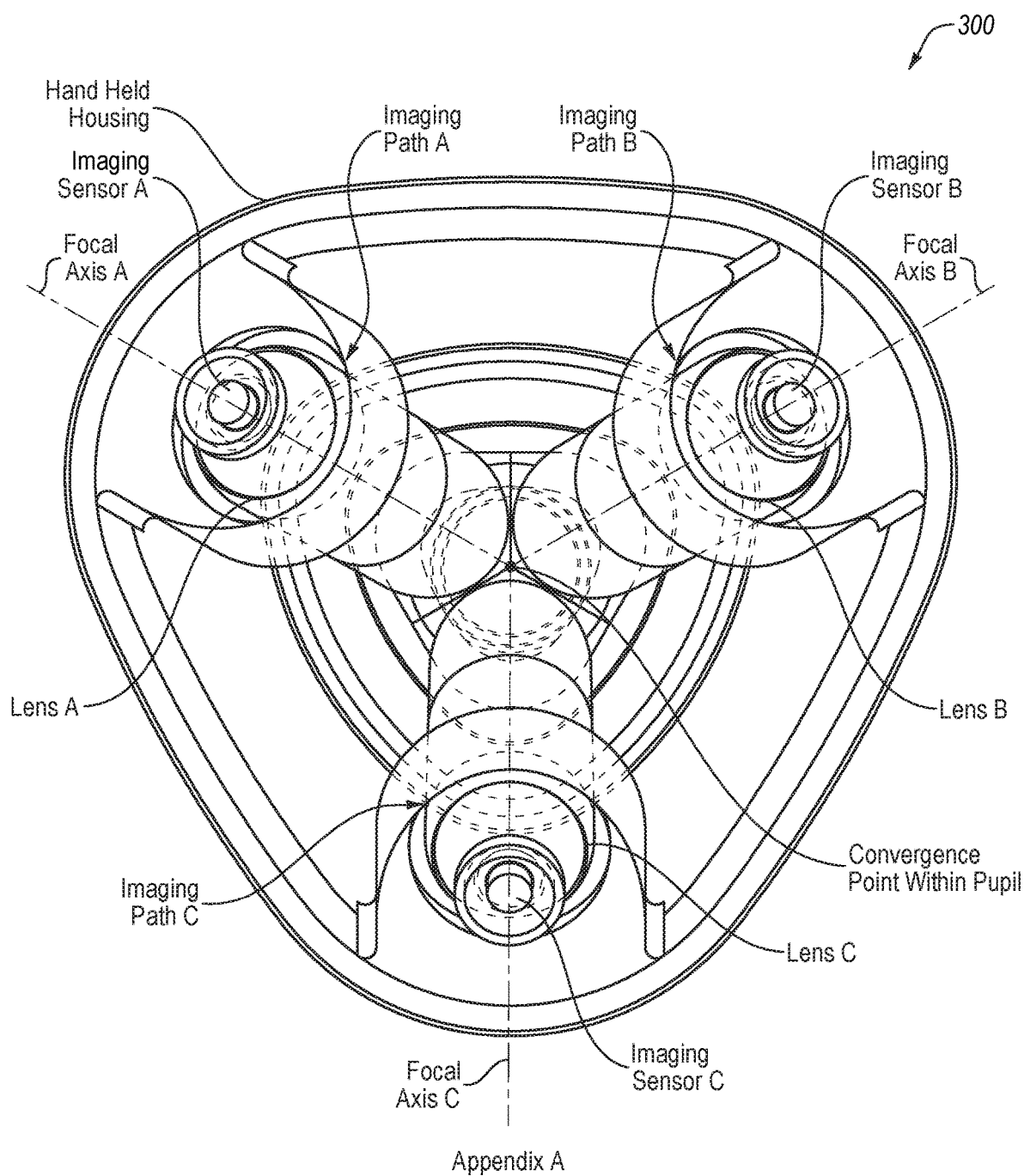
FIGS. 3A and 3B illustrate an example of a multi-channel imaging device and fields of view of multiple optical channels.
Figure 3B:
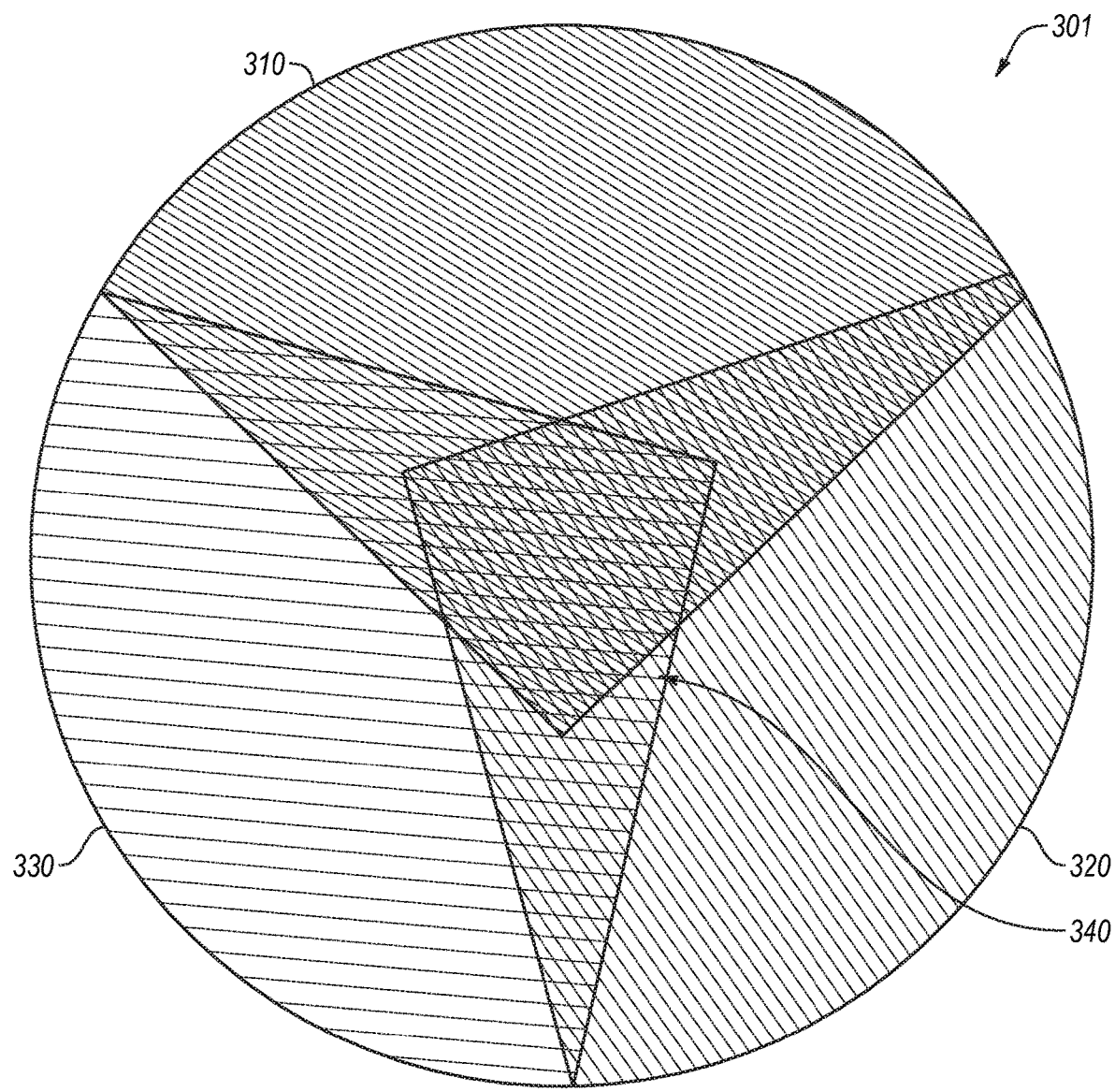

FIG. 3A illustrates an example of a multi-channel optical imaging device 300. The multi-channel imaging device 300 may include three optical channels, identified as imaging path A, imaging path B, and imaging path C. FIG. 3B illustrates an example view of an object or scene 301 with overlapping fields of view 310, 320, and 330 of three optical channels for a multi-channel optical imaging device comprising three optical channels. The object or scene 301 may be illuminated and/or imaged by the multi-channel imaging system 300 of FIG. 3A. Each optical channel may be configured to image along a respective central axis. The central axes of the optical channels may be configured to converge at a point in front of the object as shown in FIG. 2. In such a configuration, each optical channel may image a region located opposite its own position relative to the central axis, as shown in FIG. 2. The optical channel A of FIG. 3A may image the field of view 320. The optical channel B of FIG. 3B may image the field of view 330. The optical channel C of FIG. 3A may image the field of view 310. The optical channels may be configured such that the fields of view 310, 320, and 330 partially overlap. The area where the fields of view 310, 320, and 330 overlap may represent a cross channel region 340. Cross channel imaging and illumination may take place in the cross channel region 340. For example, the optical channel A may capture images from the cross channel region 340 while the optical channel B and/or the optical channel C provide illumination.

Images captured in the cross channel region 340 may be combined to create composite images. These composite images may be used to focus the optical imaging device and identify features on the object to be imaged during guidance. The composite images may be used to provide live video during alignment. The live video may be used to guide the optical imaging device to the region of the object to be imaged.

For example, in some embodiments when imaging a retina with an imaging device with three optical channels configured to provide cross-channel illumination, none of the three optical channels may be coaxial with the optical axis of the eye. In such an arrangement, the field of view of each optical channel may extend far into the periphery of the retina in one direction, but only slightly beyond the central axis of the eye in the opposite direction, so none of the three imaging pathways can independently provide an adequate live video image of the center of the retina or the periphery during approach to the eye. However, if the optical channels capture images in rapid sequence (e.g. A, B, C, A, B . . . ) the images may be combined into a composite image that covers the desired field of view. The composite images may be combined to provide guidance video for aligning the optical imaging device.

The guidance video may update on a user's display (not illustrated) as the images are captured such that the display updates sequentially according to the sequence in which the images are provided by the optical channels. The continuously updating display may follow the same sequence as the optical channels such that to the device operator, the images may appear to update in a rotating cycle. This rotating cycle of updated images may create a carousel effect on the display.

Modifications, additions, or omissions may be made to FIGS. 3A and 3B without departing from the scope of the present disclosure. For example, the fields of view 310, 320, and/or 330 may include more or fewer elements than those illustrated in FIG. 3B. For example, the cross channel region 340 may take any shape based on the number and/or orientation of cross channels to provide illumination and/or imaging.

Figure 4B:
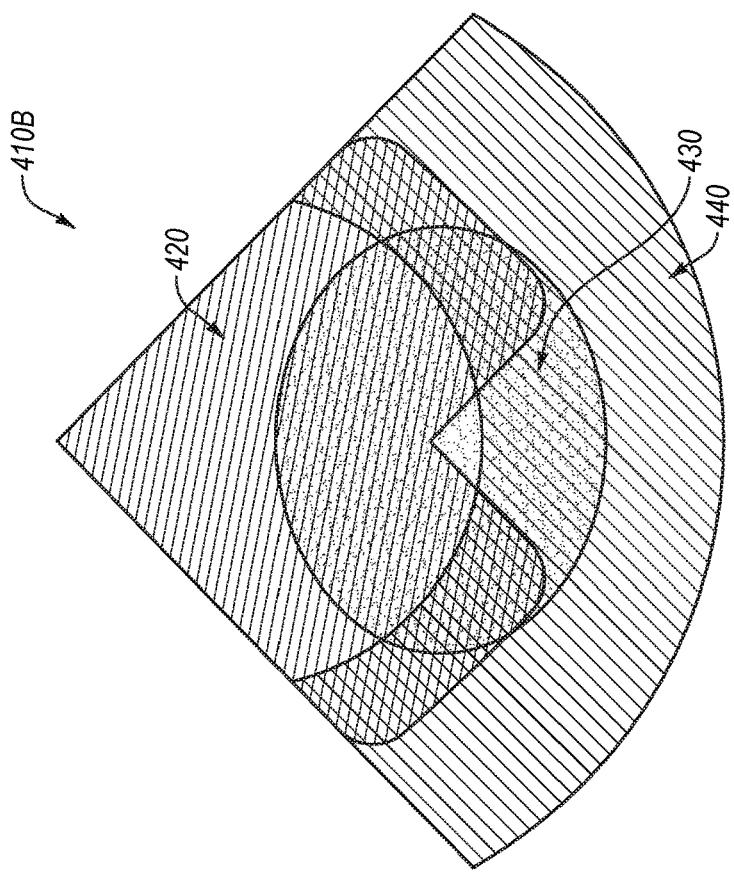
FIGS. 4A and 4B illustrate example imaging zones of optical channels.
Figure 4A:
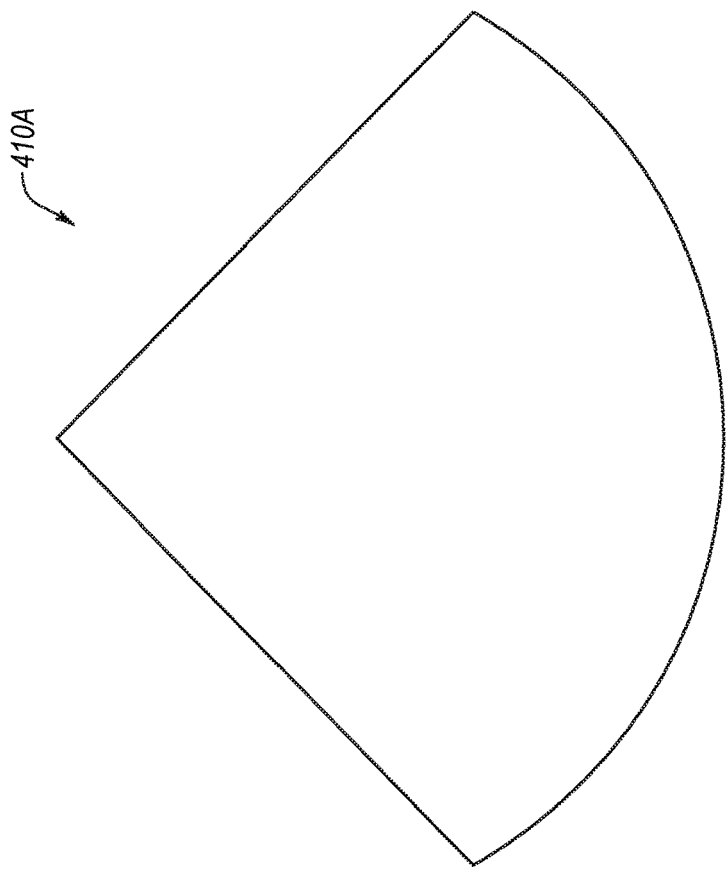

FIGS. 4A and 4B illustrate an example of a field of view 410 of an optical channel and imaging zones 420, 430, and 440 of the field of view 410. The field of view 410A may represent the total area on an object that an optical channel can image. For example, with reference to FIG. 2, the field of view 410A may correspond to the zone Y 280 imaged by the optical channel A 210. The field of view 410B may represent the same field of view illustrated in FIG. 4A but overlaid with different portions of the field of view 410B imaged and/or illuminated differently. For example, the field of view 410B may be divided into a cross channel region 420, an inner periphery region 430, and an outer periphery region 440.

The cross channel region 420 may represent a region where the fields of view of separate optical channels (including the field of view 410A) overlap. In the cross channel region 420, images may be captured by a first optical channel and illumination may be provided by a second optical channel and/or other optical channels. For example, if an optical imaging device comprises three optical channels, one optical channel may capture images in the cross channel region 420 while the other two optical channels may provide illumination in the cross channel region 420.

The other sections of the field of view 410B may include the inner periphery region 430 and the outer periphery region 440. In both the inner periphery region 430 and the outer periphery region 440, the same optical channel may or may not provide illumination and capture images. In some embodiments, both the outer and inner periphery regions 430 and 440 may provide distinct advantages in guiding and/or aligning an associated optical imaging device. For example, the outer periphery region 440 may capture a wider view of the object to be imaged and the inner periphery region 430 may be more useful when an imaging field of view is decreased (e.g., when the portion that can be imaged is clipped by the iris of the eye due to the distance of the optical imaging device away from the eye).

The cross channel region 420, the inner periphery 430, and the outer periphery 440 may be imaged simultaneously or in isolation. For example, in a multi-channel optical imaging device including optical channels A, B, and C where optical channel C can capture images of the field of view 410B, optical channel A and/or optical channel B may illuminate the cross channel region 420 while optical channel C may capture images from the cross channel region 420. Simultaneously, optical channel A and/or optical channel B may illuminate the inner periphery and/or outer periphery of its own respective field of view and capture images from its inner periphery and/or outer periphery while also illuminating the cross channel region 420 of the optical channel C. As another example, in a multi-channel optical imaging device including optical channels A, B, and C, optical channel A and/or optical channel B may illuminate the cross channel region 420 while optical channel C may capture images from the cross channel region 420. Simultaneously, optical channel C may illuminate and capture images in the inner periphery 430 and/or the outer periphery 440 such that the optical channel C may capture an image that includes the cross channel region 420 as well as the inner periphery 430 and/or the outer periphery 440 while avoiding artifacts in the image due to the use of the beneficial cross-channel illumination from optical channels A and/or B. In such an example, an image of the entire field of view 410B for one optical channel may be captured to facilitate alignment and/or guidance of the imaging device. In these and other embodiments, the peripheral illumination from optical channel C may not cause artifacts in the image, and the cross-channel illumination from optical channels A and/or B may not cause artifacts in the image.

In the example application of imaging a retina, the cross channel region 420 may be illuminated with red or infrared light which causes less discomfort than white light to the center of the retina while the peripheral regions may be illuminated with white light (or some other color of light, including red or infrared light).

Modifications, additions, or omissions may be made to the fields of view 410A and/or 410B without departing from the scope of the present disclosure. For example, the fields of view 410A and/or 410B may include more or fewer elements than those illustrated in FIGS. 4A and 4B. For example, the cross channel region 420 may take any shape based on the number and/or orientation of cross channels to provide illumination and/or imaging.

Figure 5:
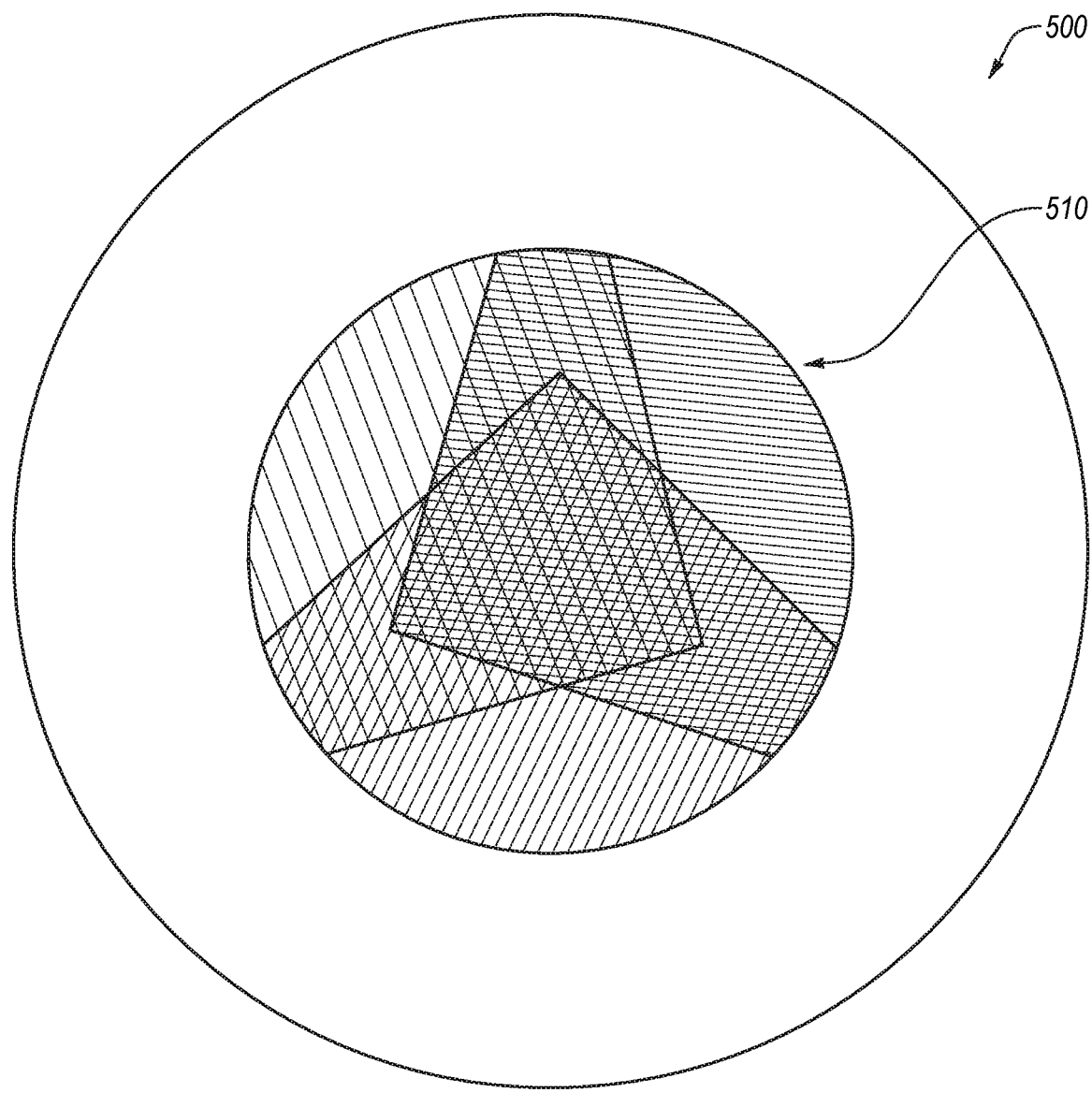
FIG. 5 illustrates an example of a cross channel region where the imaging zones of three optical channels overlap.

FIG. 5 illustrates an example of a central guidance view 510 for a multi-channel optical imaging device comprising three optical channels. The central guidance view 510 is formed of composite images from part or all of the cross channel regions of the fields of view of the optical channels. The central guidance view 510 may be the portion of the fields of view of the optical channels that is used to guide and focus the optical imaging device. For example, certain portions of the image may be discarded or the entire image may be used when providing the central guidance view 510.

Images from the three optical channels may be combined via stitching, stamping, or another process to create composite images. The composite images may be created quickly enough to create a sense of smooth, continuous video. For example, each optical channel may capture 45 images per second and optical channels A, B, and C may capture images sequentially (e.g. A, B, C, A, B . . . ). Then, images from the three optical channels may be stitched together to create composite images. Three sequential images from the three optical channels may be combined into a composite image to form a frame of a video that may run at 15 frames per second, giving a sense of smooth, continuous video. This video may then be used to focus and align the optical imaging device as well as provide confirmation of centration. While described as operating at a capture rate of 45 images per second and video at 15 frames per second, any rate may be used. For example, the images may be captured at any rate from 10 images per second to 180 frames per second, yielding videos from 5 to 60 frames per second.

In some embodiments, when imaging a retina, the composite central guidance view 510 may give a user a continuous video of central retinal features such as the optic nerve, macular blood vessels, etc. This video may be used to guide the optical imaging device to the center of the retina in order to align the optical imaging device and/or perform manual focus or autofocus functions based on the landmarks in or near the center of the retina, such as the optic nerve, macular blood vessels, etc. For such guidance video, red or infrared light may be used to avoid discomfort which may be caused by white light to provide illumination during image capture.

Modifications, additions, or omissions may be made to the composite central guidance view 510 without departing from the scope of the present disclosure. For example, the composite central guidance view may include more or fewer elements than those illustrated in FIG. 5. For example, the composite central guidance view 510 may take any shape based on the number and/or orientation of cross channels to provide illumination and/or imaging.

Figure 6:
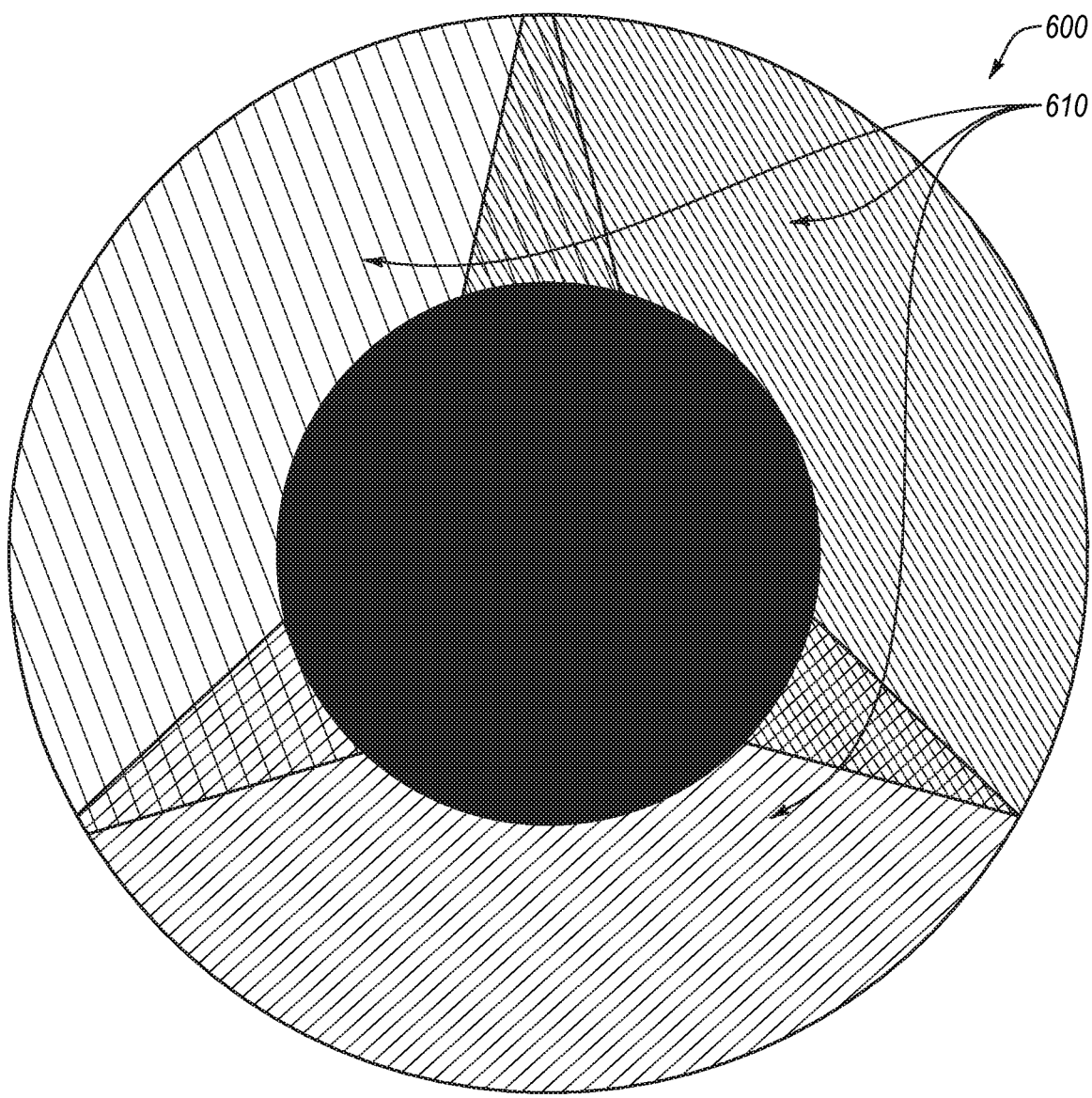
FIG. 6 illustrates an example of illumination of an outer periphery by three optical channels.

FIG. 6 illustrates an example of an outer periphery region 610 of a field of view 600 of a multi-channel optical imaging device comprising three optical channels. The combined field of view 600 represents the total combined area visible to all the optical channels. The periphery of each optical channel is the region where imaging and illumination are provided through the same optical channel, as opposed to the cross channel region where imaging and illumination are provided through disparate optical channels. An optical channel may provide illumination in the cross channel region and capture images in its periphery, and may occur in series or simultaneously. Thus, for example, if optical channel A is providing illumination for optical channel B to image in the cross channel region, optical channel A may simultaneously capture images from its outer periphery. Images from the outer periphery may be used in centering the optical imaging device.

For example, when imaging a retina, the outer periphery 610 of the optical device may provide images of three sections of retina that may be relatively rotationally symmetric if the device is centered. This rotational symmetry may allow the user of the optical imaging device to properly center the optical device on the eye. The three outer peripheral retinal zones could be shown to the user in a direct representation, in a distorted representation (e.g., compressed in a centrifugal fashion relative to the center of the guidance display), or in an indirect manner (graphics that provide the user with an indication of centration based on the three outer peripheral zones rather than showing those zones directly, such as status bars, a dot within a circle, etc.). In these and other embodiments, image analysis may be performed on the images of the peripheral zones to provide indications of relative centration when generating the indirect graphics.

The outer periphery 610 may also be used to guide the optical device to a useful working distance for imaging. For example, if the optical imaging device is not close enough to the eye, the outer periphery 610 of the fields of view of the optical channels of the optical device may not fall within the patient's pupil, and illumination on the outer periphery 610 will not enter the eye due to being truncated by the iris. If illumination to the outer periphery 610 does not enter the pupil, images from the outer periphery 610 may be obscured. In some embodiments, the images from the outer periphery 610 of the optical device may not be shown to the user at scale. For example, they may be compressed or simplified to simply provide a gross sense of centration.

Modifications, additions, or omissions may be made to the outer periphery 610 without departing from the scope of the present disclosure. For example, the outer periphery 610 may include more or fewer elements than those illustrated in FIG. 6. For example, the outer periphery 610 may take any shape based on the number and/or orientation of cross channels to provide illumination and/or imaging.

Figure 7:
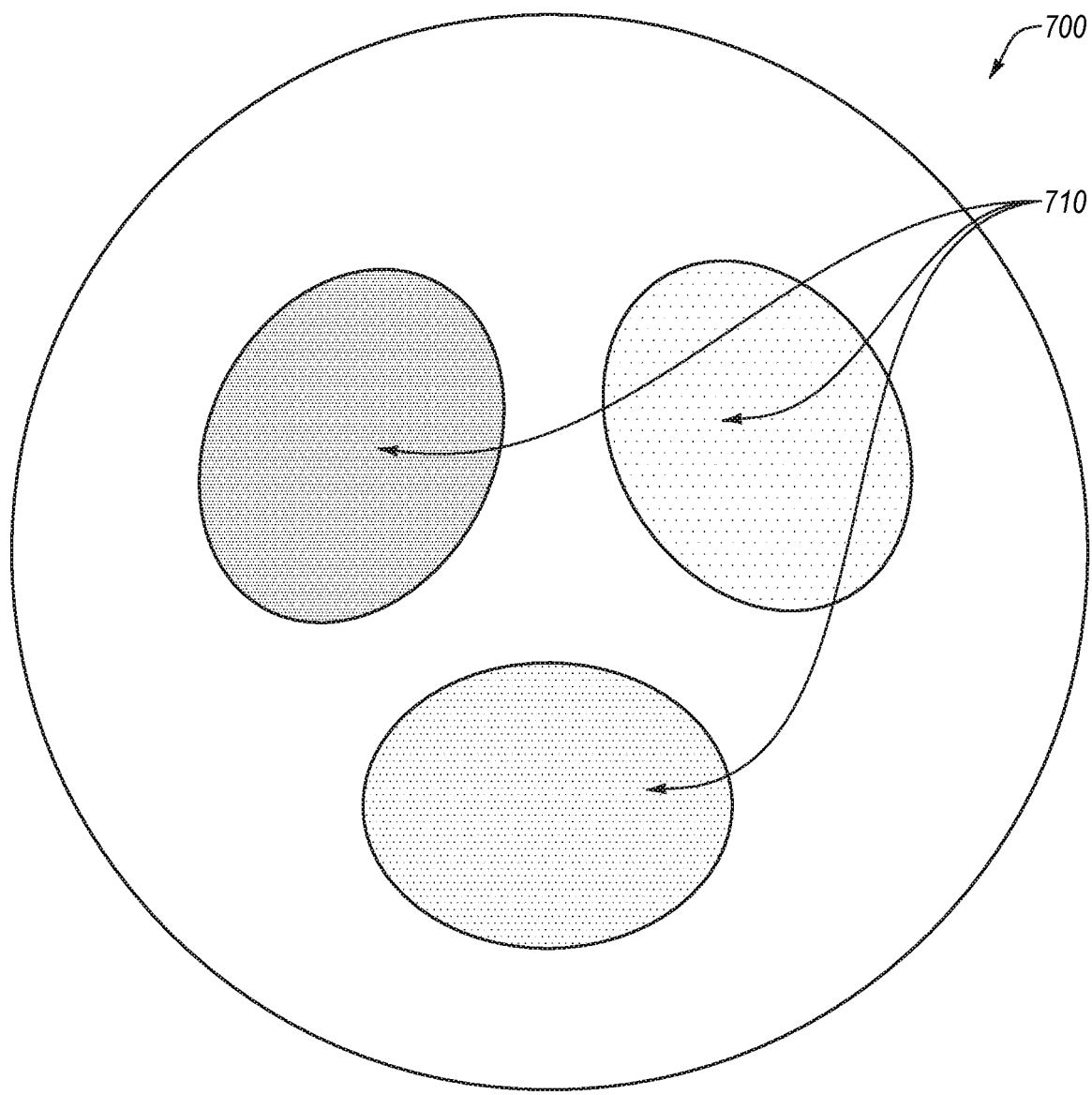
FIG. 7 illustrates an example of illumination of an inner periphery by three optical channels.

FIG. 7 illustrates an example of an inner periphery 710 of an optical imaging device comprising three optical channels. The combined field of view 700 represents the total combined area visible to all the optical channels. Like the outer periphery of an optical channel, the inner periphery 710 of an optical channel may be imaged and illuminated through the same optical channel. The inner periphery 710 may be used to center an optical imaging device. For example, when imaging a retina, the inner peripheries of three optical channels may image three sections of retina that may be relatively rotationally symmetric if the device is centered. Using the inner periphery 710 may be advantageous over using the outer periphery for centering when the field of view is decreased because the inner periphery is closer to the center of the field of view than the outer periphery. For example, when imaging a retina, inner peripheral guidance may be more useful than outer peripheral guidance if a patient's pupil is too small to image the outer periphery or if the device is used in a non-contact manner, shrinking the field of view. In some embodiments, the images from the inner peripheries of the optical channels may not be shown to the user at scale. For example, the images may be compressed or simplified to simply provide a gross sense of centration. In some embodiments, a user may have the option of switching between inner and outer peripheral guidance. For example, the illumination of the inner vs. outer periphery may be manually turned on or off such that one or the other or both between the inner and outer peripheral guidance may be used.

Modifications, additions, or omissions may be made to the inner periphery 710 without departing from the scope of the present disclosure. For example, the inner periphery 710 may include more or fewer elements than those illustrated in FIG. 7. As another example, the inner periphery 710 may take any shape based on the number and/or orientation of cross channels to provide illumination and/or imaging.

Figure 8A:
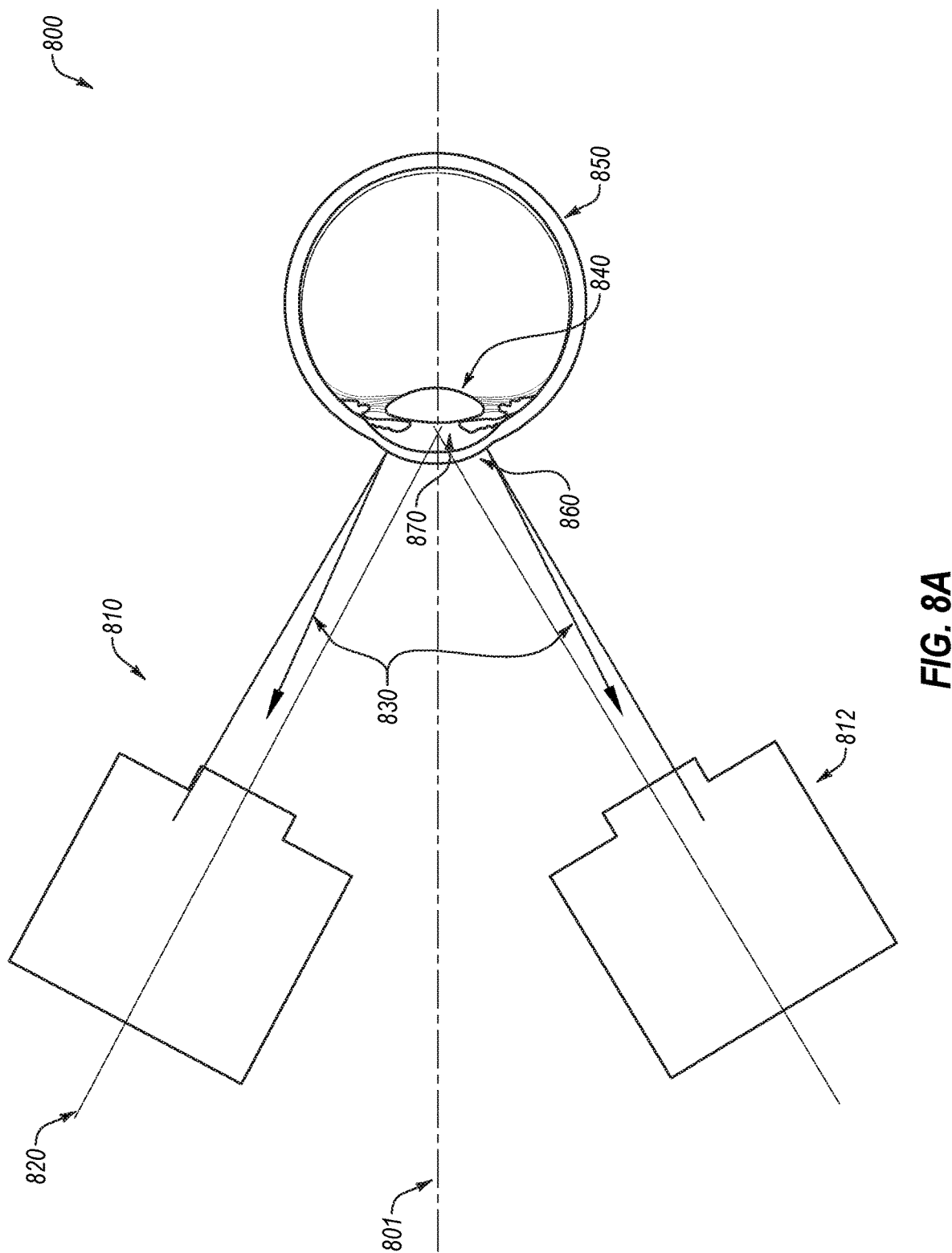
FIGS. 8A and 8B illustrate an example implementation of using reflections off a cornea of optical channel illumination to align an optical imaging device.
Figure 8B:
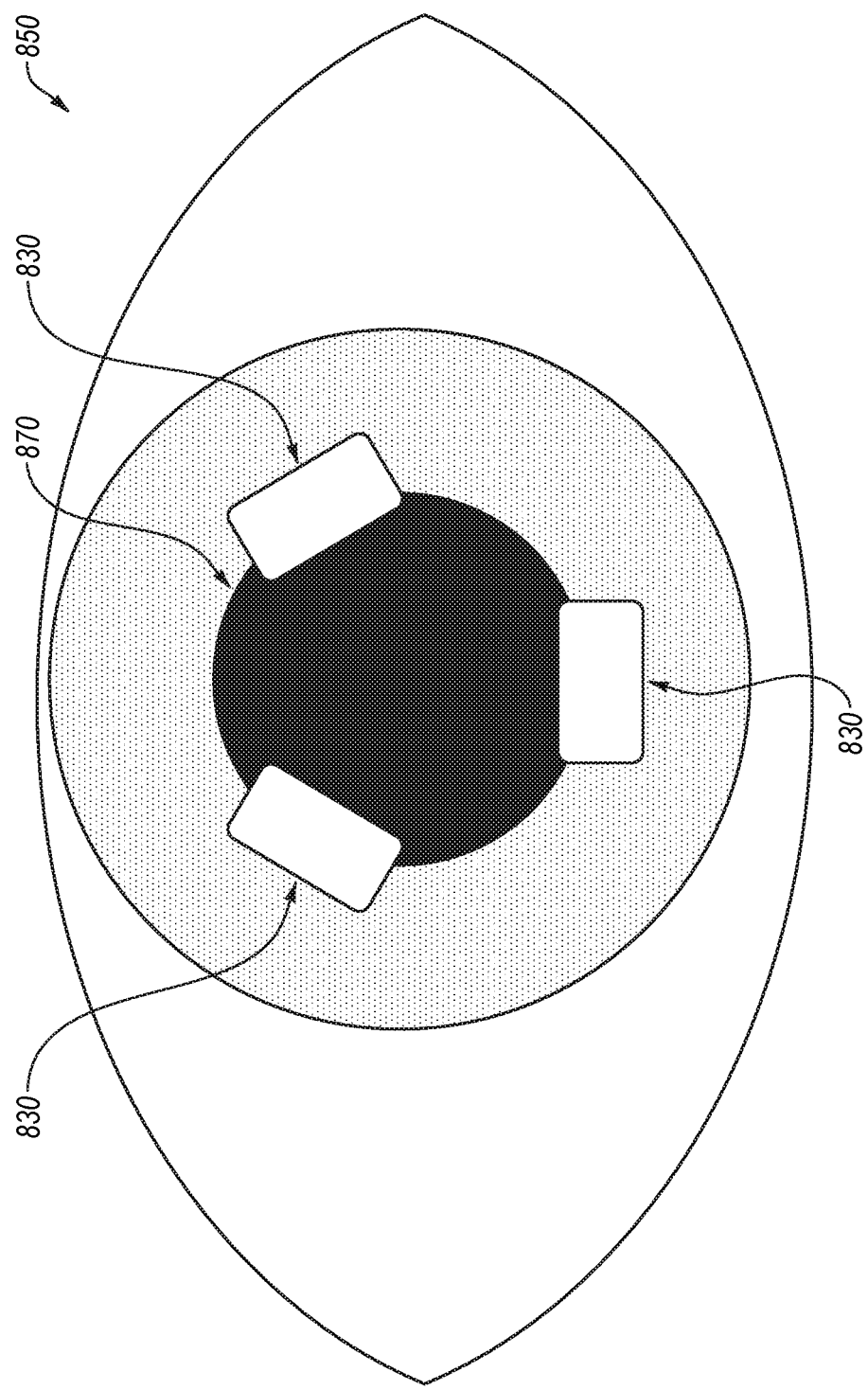

FIGS. 8A and 8B illustrate an example of corneal reflections 830 of illumination from optical channels. FIG. 8A gives a side view of optical channel A 810 and optical channel B 812 illuminating an eye 850. FIG. 8B illustrates a front view of an eye with reflections 830. As illustrated in FIGS. 8A and 8B, a configuration 800 of the optical channel A 810 and the optical channel B 812 may cause reflections 830 off of an eye 850. Illumination from optical channel A may be directed so as to create a reflection 830 off of the cornea 860 that is visible to optical channel A. The optical channel A 810 is used as an example, but the same description may apply to the optical channel B 812. The illumination may be directed such that the reflection 830 is peripheral enough not to obscure the center of the field of view, but central enough that the light creates a sharp, distinct reflection 830 off of the cornea 860. FIG. 8B illustrates the eye 850 with reflections 830 from three optical channels. Such reflections 830 may provide direct visual feedback through guidance video that assists in alignment of the device. For example, optical channels may be directed such that the reflections 830 sit at points around the pupil 870 when the optical imaging device is properly aligned as shown in FIG. 8B.

The illumination from the optical channels of the optical imaging device may be directed so that it creates sharp, distinct reflections off a patient's cornea 860 at a useful working distance from a patient's eye. By way of example and not limitation, a useful working distance may be a distance that is close enough for image capture and/or close enough that minimal additional movement occurs to position the optical imaging device for image capture. In some embodiments, the corneal reflections 830 may be used to guide the optical imaging device to a useful working distance and/or to center the optical imaging device. A user may move the optical imaging device and use the corneal reflections 830 to guide the optical imaging device and to confirm that the optical imaging device is at a useful working distance for imaging and centered on the eye 850.

In some embodiments, the illumination from the optical channels of the optical imaging device may be directed so that the corneal reflections 830 may appear during early guidance when the optical imaging device is at a first distance from the eye 850, followed by the corneal reflections 830 disappearing during late guidance when the optical imaging device is brought to a second distance nearer the eye 850. The illumination that causes the corneal reflections 830 at the first distance may illuminate the peripheries inside the eye 850 when the optical device is brought to the second distance closer to the eye 850. Put another way, the optical channels may be directed such that at the first distance from the eye 850 the peripheral illumination from the optical channels may cause corneal reflections 830 and at the second distance nearer the eye 850 the peripheral illumination from the optical channels may illuminate the periphery of the optical imaging device as shown in FIGS. 6 and 7.

In one embodiment, optical channels A, B, and C may be arranged to cause reflections 830 at three points around a patient's pupil 870. The optical channels A, B, and C may capture images and illuminate sequentially (e.g. A, B, C, A, B . . . ) such that the reflections 830 appear to rotate, creating a carousel effect that is visible on the display (not illustrated) of the optical device.

Modifications, additions, or omissions may be made to the configuration 800 of the optical channels 810, 812 without departing from the scope of the present disclosure. For example, the reflections 830 on the cornea 860 may include more or fewer elements than those illustrated in FIGS. 8A and 8B. For example, the reflections 830 may take any shape based on the number and/or orientation of optical channels to provide illumination and/or imaging.

In some embodiments, when imaging an eye, a fixation target (not illustrated) may be placed within a central channel that fits between the three optical channels. This fixation target may blink or may be synchronized with the illumination of the three optical channels. This fixation target may include optical lenses such that the target appears at a set distance in front of an emmetropic patient. The fixation target may remain visible independent of illumination and image capture performed by the three optical channels.

The advantage of this type of fixation target is that none of the three optical channels has to continuously illuminate the eye, allowing for cross channel illumination and imaging. If one optical channel continuously illuminated the eye to serve as a fixation target, it might generate detrimental imaging artifacts within the images of that channel, which may result in misalignment or other problems in guiding the imaging device into position for imaging the eye.

In some embodiments, in implementation, the inner periphery illumination and images may be used for initial guidance as the imaging device is farther away from the eye, followed by outer periphery illumination and images for guidance and centering as the imaging device comes closer to the eye, followed by cross-channel illumination and imaging for focus and centering in the final alignment and guidance of the imaging device. As another example of implementation, the reflections from the outer periphery illumination may be used for initial guidance as the imaging device is farther away from the eye, followed by inner and outer peripheral illumination being used for guidance as the imaging device comes closer to the eye, and inner periphery illumination and images and cross channel illumination and images being used for the final alignment and guidance of the imaging device. As another example of implementation, cross channel images may be used during the initial approach for gross positioning, centration and focusing, followed by outer peripheral illumination to refine centration prior to image capture. As an additional example of implementation, cross channel images may be displayed concurrently with outer periphery images to allow both gross visualization and focusing using the cross channel images as well as confirmation of centration using the outer peripheral illumination. As another example of implementation, cross channel images may be displayed concurrently with indirect graphics representing the outer periphery images to allow both gross visualization and focusing using the cross channel images as well as confirmation of centration using the indirect graphs representing the outer peripheral images.

In some embodiments, the multi-channel imaging system as illustrated in FIGS. 2, 3A and 8A may include a computing device (not illustrated). Such a computing device may be configured to facilitate the performance of the operations described herein, such as capturing images, turning on or off illumination sources, image processing, video display, etc. Such a computing device may include a processor, a memory, etc. and may be in communication with and/or part of the multi-channel imaging system.

Generally, the processor may include any suitable special-purpose or general-purpose computer, computing entity, or processing device including various computer hardware or software modules and may be configured to execute instructions stored on any applicable computer-readable storage media. For example, the processor may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

It is understood that the processor may include any number of processors distributed across any number of networks or physical locations that are configured to perform individually or collectively any number of operations described herein. In some embodiments, the processor may interpret and/or execute program instructions and/or processing data stored in the memory. By interpreting and/or executing program instructions and/or process data stored in the memory, the device may perform operations, such as the operations performed by the retinal imaging device described in the present disclosure.

The memory may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. In these and other embodiments, the term "non-transitory" as used herein should be construed to exclude only those types of transitory media that were found to fall outside the scope of patentable subject matter in the Federal Circuit decision of *In re Nuijten,* 500 F.3d 1346 (Fed. Cir. 4007). In some embodiments, computer-executable instructions may include, for example, instructions and data configured to cause the processor to perform a certain operation or group of operations as described in the present disclosure.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method. For example, the dashed lines of the illumination paths and imaging paths are not meant to reflect an actual optical design, but are illustrative of the concepts of the present disclosure.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the term "about" or "approximately" should be interpreted to mean a value within 10% of actual value.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A method of aligning an imaging device with respect to an object, the imaging device comprising two or more optical channels, the method comprising:
   aiming the two or more optical channels at corresponding overlapping zones of the object such that the two or more optical channels are oriented at different angles relative to each other and off-axis relative to a central axis of the imaging device; and
   guiding or focusing the imaging device relative to the object using composite images created by:
      combining separate images from the two or more optical channels,
      at a first distance from the imaging device to the object, illuminating an inner periphery region of the object to create reflection,
      at a second distance from the imaging device to the object, which second distance is shorter than the first distance, illuminating an outer periphery region of the object,
      performing initial guidance of the imaging device based on illumination and images of the inner periphery region of the object, while the imaging device is disposed at the first distance from the object,
      after the initial guidance, performing second guidance of the imaging device based on illumination and images of the outer periphery region of the object, as the imaging device is disposed at the second distance, and
      after the second guidance, performing third guidance of the imaging device based on illumination and images of a cross-channel region of the object, wherein the object is an eye and the cross-channel region includes at least one of the overlapping zones.

2. The method of claim 1, further comprising centering the imaging device using images from outer and inner peripheries of fields of view of the optical channels.

3. The method of claim 2, wherein the images from the outer and inner peripheries are used to generate the composite images.

4. The method of claim 1, wherein the imaging device is aligned using corneal reflections of illumination from the two or more optical channels.

5. The method of claim 4, wherein a fixation target is located between the optical channels, the fixation target including a target for the eye to focus upon while the eye is imaged.

6. The method of claim 1, wherein the two or more optical channels include a first and a second optical channel, and wherein guiding or focusing the imaging device comprises:
   illuminating a cross-channel region of the first optical channel via the second optical channel; and
   capturing one of the separate images as a cross-channel image of the cross-channel region of the first optical channel via the first optical channel while the second optical channel is illuminating the cross-channel region,
   wherein the cross-channel image is used to generate the composite images.

7. The method of claim 6, further comprising illuminating at least one of an outer and an inner periphery of a field of view of the first optical channel while the second optical channel illuminates the cross-channel region.

8. The method of claim 6, further comprising:
   after capturing the cross-channel image, illuminating a second cross-channel region of the second optical channel via the first optical channel;
   capturing a second cross-channel image of the second cross-channel region of the second optical channel via the second optical channel while the first optical channel is illuminating the second cross-channel region; and
   generating a second composite image using the second cross-channel image.

9. The method of claim 8, further comprising updating a display previously presenting one or more of the composite images to the second composite image to create a video on the display.

10. The method of claim 9, further comprising repeatedly generating additional composite images and updating the display with the additional composite images, the updating the display creating a carousel effect as different regions of the video are updated based on which of the two or more optical channels captures sub-images contributing to the additional composite images.

11. The method of claim 1, wherein guiding or focusing the imaging device comprises:
    performing final guidance or focusing based on a third set of the composite images representing at least a cross channel region of the eye as the imaging device is at a different distance away from the eye.

12. The method of claim 1, wherein guiding or focusing the imaging device comprises:
    performing the initial guidance based on a first set of the composite images representing at least cross channel regions of an eye as the imaging device is disposed at the first distance away from the eye; and
    performing, as the third guidance, final guidance or focusing based on a second set of the composite images representing at least an outer periphery region of the eye as the imaging device is at disposed at the second distance away from the eye closer than the first distance.

13. The method of claim 1, wherein guiding or focusing the imaging device comprises concurrently displaying both a first subset of the composite images representing cross channel regions of an eye and a second subset of the composite images representing an outer periphery region of the eye.

14. The method of claim 1, wherein guiding or focusing the imaging device comprises concurrently displaying both a first subset of the composite images representing cross channel regions of the eye and an indirect graphic based on the outer periphery region of the eye.

15. The method of claim 14, wherein the indirect graphic includes at least one of status bars and a dot within a circle.

16. A method of aligning an imaging device with respect to an object, the imaging device comprising two or more optical channels, the method comprising:
    aiming the two or more optical channels at corresponding overlapping zones of the object such that the two or more optical channels are oriented at different angles relative to each other and off-axis relative to a central axis of the imaging device; and
    guiding or focusing the imaging device relative to the object using composite images created by:
       combining separate images from the two or more optical channels,
       at a first distance from the imaging device to the object, illuminating a peripheral region of the object to create reflection, and at a second distance from the imaging device to the object, which second distance is shorter than the first distance, illuminating the peripheral region of the object to illuminate a periphery of the imaging device, wherein guiding or focusing the imaging device comprises:

performing initial guidance based on corneal reflections of illumination from the two or more optical channels off of a cornea of an eye as the imaging device is the first distance away from the eye, performing secondary guidance based on a first set of the composite images representing at least inner and outer periphery regions of the eye as the imaging device transitions from the first distance away from the eye to the second distance away from the eye closer than the first distance, and performing final guidance or focusing based on a second set of the composite images representing both a cross channel region and the inner periphery region of the eye as the imaging device is at the second distance away from the eye.

17. The method of claim 16, wherein a fixation target is located between the optical channels, the fixation target including a target for the eye to focus upon while the eye is imaged.

18. The method of claim 16, wherein the images from the outer and inner periphery regions are used to generate the composite images.

19. The method of claim 16, wherein the guiding or focusing is performed manually be a user of the imaging device.

20. The method of claim 17, wherein the fixation target is synchronized with illumination of the first and second optical channels.

* * * * *